US00PP18833P2

(12) United States Plant Patent
Randag

(10) Patent No.: US PP18,833 P2
(45) Date of Patent: May 27, 2008

(54) CALLA LILY PLANT NAMED 'ODESSA'

(50) Latin Name: *Zantedeschia sprengeri*
Varietal Denomination: Odessa

(75) Inventor: Cecilius Jan-Jochem Randag, Bosweg (NL)

(73) Assignee: Sande BV, CJ't Zand (NL)

( * ) Notice: Subject to any disclaimer, the term of this patent is extended or adjusted under 35 U.S.C. 154(b) by 0 days.

(21) Appl. No.: 11/644,799

(22) Filed: Dec. 22, 2006

(51) Int. Cl.
*A01H 5/00* (2006.01)

(52) U.S. Cl. ..... Plt./490
(58) Field of Classification Search ..... Plt./490, Plt./263
See application file for complete search history.

*Primary Examiner*—Wendy C. Haas
(74) *Attorney, Agent, or Firm*—The Webb Law Firm

(57) ABSTRACT

'Odessa' is a new variety of calla lily having a flower with a purple colored spathe producing 2-15 flowers per tuber. The flower stems are about 60 cm in height. The leaves are green with whitish spots and they have a leathery texture.

2 Drawing Sheets

Botanical classification: *Zantedeschia sprengeri.*
Varietal denomination: 'Odessa'.

BACKGROUND OF THE NEW PLANT

The present invention comprises a new and distinct cultivar of calla lily, botanically known as *Zantedeschia sprengeri* and hereinafter referred to by the cultivar name 'Odessa'.

'Odessa' is a product of a planned breeding program which had the objective of creating *Zantedeschia* hybrids for cut flower production in a wide range of colors with a large, classic flower shape. The breeding program began in 1989 and the new cultivar is a seedling selected from the crossing of a *Zantedeschia sprengeri* seedling C02029 (female parent, unpatented) with *Zantedeschia sprengeri* seedling C02021 (male parent, unpatented). 'Odessa' was selected in 2001 by the inventor C. J. J. Randag in CJ't Zand, The Netherlands as one flowering plant within the progeny of the stated cross.

The first act of asexual reproduction of 'Odessa' by tissue culture was performed by the inventor in August 2001 in CJ't Zand, The Netherlands. Subsequent asexual reproduction by tissue culture at the same location has demonstrated that the combination of characteristics as herein disclosed for the new cultivar are retained and reproduced true to type through successive generations of asexual reproduction.

The following observations, measurements and comparisons describe plants grown in CJ't Zand, The Netherlands under greenhouse conditions which approximate those generally used in horticultural practice. Color references are made to the R.H.S. Colour Chart of The Royal Horticulture Society of London, except where general color terms of ordinary significance are used.

The present invention has not been evaluated under all possible environmental conditions. The phenotype may vary with variation in environment without a change in the genotype of the plant.

The following traits have been repeatedly observed and determined to basic characteristics of 'Odessa' which, in combination, distinguish this calla lily as a new and distinct cultivar:

1. Dark purple spathe;
2. Fast forcing time; and
3. High flower production.

Table 1 provides similarities and differences of 'Odessa' to its parents and 'Black Star' (U.S. Plant Pat. No. 14,844).

TABLE 1

| Odessa | Similarities | Differences |
|---|---|---|
| C02029 (female parent) | Leave shape | Number of spathes. |
| C02021 (male parent) | Leave shape | Spots on leaf; and Color of spathe. |
| 'Black Star' (PP14,844) | Leave shape | No purple line on leaf margin; Spathe shape; and Color of peduncle. |

BRIEF DESCRIPTION OF THE DRAWINGS

The accompanying photographic drawings illustrate the new variety, with the colors being as nearly true as is possible with color illustrations of this type.

DESCRIPTION OF THE PLANT

Figure 1:
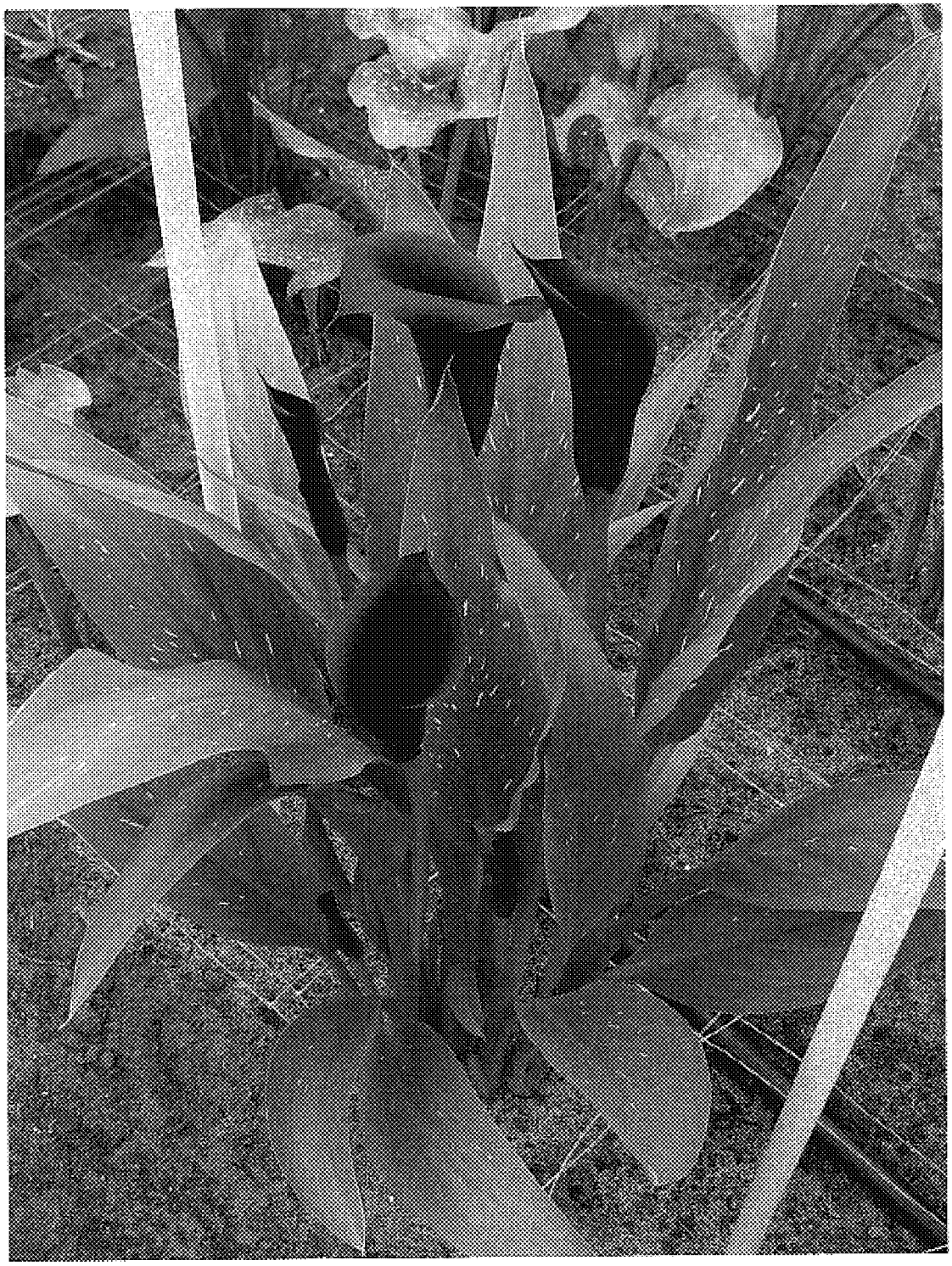
FIG. 1 is a photograph of the flowers and leaves.
Figure 2:
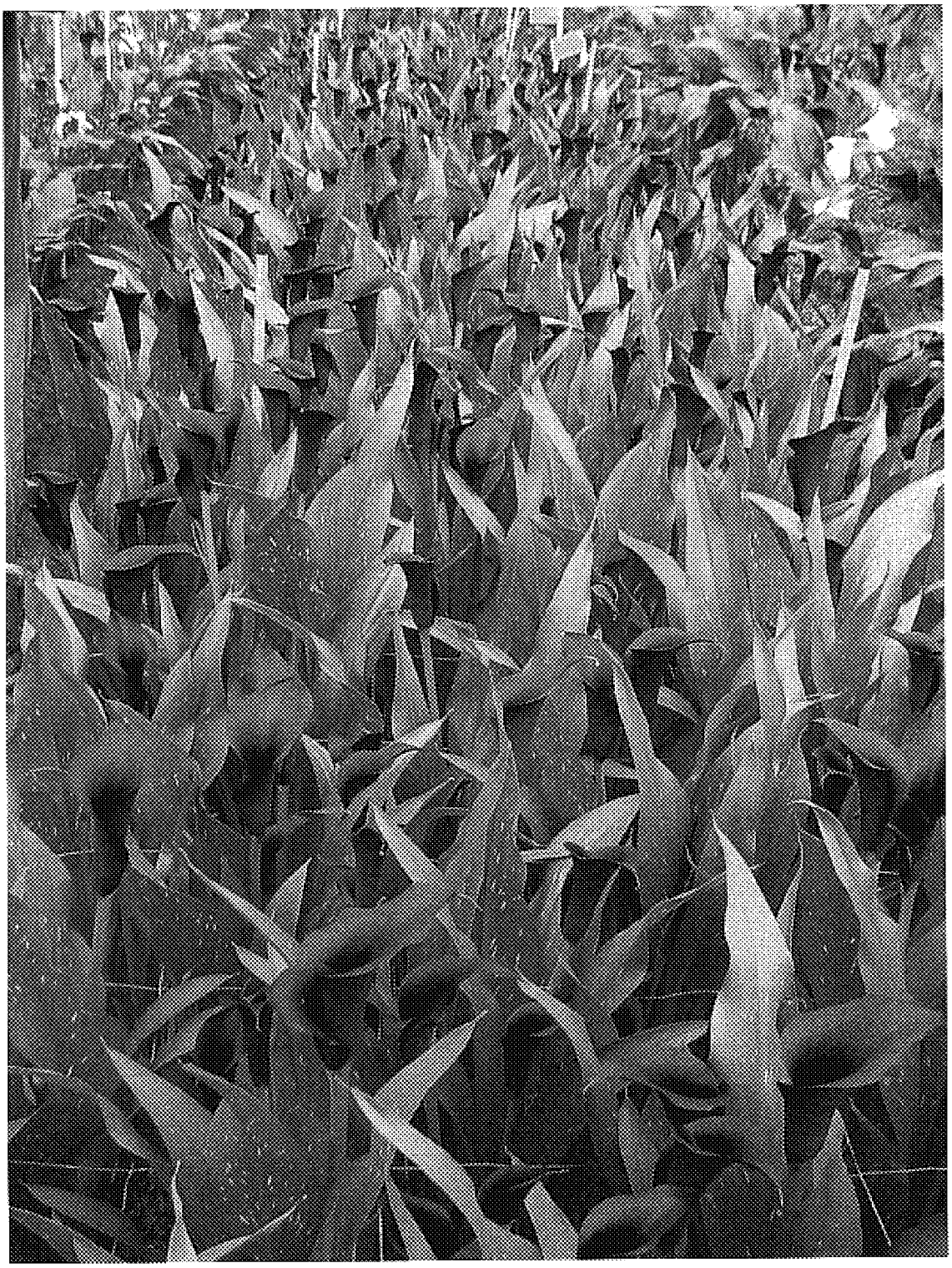
FIG. 2 is a photograph of the stability of the crop after tissue culture.

Size:
*Height of the leaf canopy above the soil.*—60-65 cm.
*Height of top of inflorescence above the soil.*—60-65 cm.
*Diameter.*—30-40 cm.

Form: Erect.

Number of inflorescences per tuber:
*Circumference of 9-12 cm.*—2-4 inflorescences.
*Circumference of 12-15 cm.*—4-7 inflorescences.
*Circumference of 15-18 cm.*—7-15 inflorescences.

Branches:
*Character.*—Many like the variety 'Chrystal Blush' (unpatented).
*Color.*—Between Yellow-Green Group RHS 146A and 146B, with spots of Red Group RHS 53A.

Leaves:
*Size.*—Width: 7-8 cm. Length: 25-30 cm.
*Number per plant.*—20-30.
*Shape.*—Elliptic.
*Color.*—Upper surface: Green Group RHS 137A-137B. Lower surface: Green Group RHS 137A-137B.
*Margin.*—Wavy.
*Veins.*—Configuration: Pinnate. Color: Yellow-Green Group RHS 147A.
*Surface texture.*—Leathery.
*Petiole.*—Length: 10-30 cm. Color: The basis Green-White Group RHS between 157A and 157B and the upper part between Yellow-Green Group RHS 144A and 144B.

Roots:
*Color.*—White.
*Branching.*—Similar to other *Zantedeschia* varieties.

INFLORESCENCE

Spathe:
*Size.*—Length: 6-15 cm. Width: 4-7 cm.
*Color.*—Upper surface: Varies between Purple Group RHS 79A and Black Group RHS 202A. Lower surface: Varies between Purple Group RHS 79A and Black Group RHS 202A.
*Veins.*—Color: Varies between Purple Group RHS 79A and Black Group RHS 202A.
*Shape.*—Cupped.

Spadix:
*Size.*—Length: 10-25 mm. Diameter: 2-5 mm.
*Color.*—Varies between Purple Group RHS 79A and Black Group RHS 202A.
*Position relative to spathe.*—Upright.

Peduncle:
*Size.*—Length: 30-65 cm. Diameter: 6-10 mm.
*Color.*—Upper part varies between Yellow-Green Group RHS 144A and 144B. Lower part Green-White Group RHS 157D.

Reproductive organs:
*Location of female organs.*—Basal position of the spadix.
*Location of male organs.*—Upper position of the spadix.
*Perianth.*—Conspicuous.
*Stamens.*—Not visible before pollen release. Number: More than 50.
*Pollen.*—Amount: Similar to 'Schwarzwalder' (U.S. Plant Pat. No. 11,001). Color: Varies between White Group RHS 155A and 155B.

Anther:
*Shape.*—Round wire-like.
*Length.*—Less than 1 mm.
*Color.*—Between White Group RHS 155A and RHS 155B.

Filament:
*Length.*—Less than 1 mm.
*Color.*—Between White Group RHS 155A and 155B.

Pistil:
*Number.*—20 to 40.
*Length beyond perianth.*—About 1 mm.
*Stigma.*—Shape: Round. Size: Less than 1 mm.
*Style.*—Length: Less than 1 mm. Color: Between Purple Group RHS 79A and Black Group RHS 202A.
*Ovaries.*—Texture: Smooth. Length: Between 1 to 10 mm. Width: Between 1 to 10 mm. Color: Top: Between Purple Group RHS 79A and Black Group RHS 202A. Bottom: Green-White Group RHS 157C and 157D.

Seeds:
*Length.*—4-7 mm.
*Width.*—3-6 mm.
*Color.*—Between Purple Group RHS 79A and Black Group 202A.
*Amount.*—Between 1-50.

Disease resistance: None observed.
Pest resistance: None observed.
Heat tolerance: No heat tolerance.
Hardiness: Not hardy.
Flowering: Tubers planted in a greenhouse in The Netherlands in February produce flowers in April. Tubers planted outdoors in The Netherlands in May produce flowers in July.
Lastingness: About two weeks on the plant.
Fragrance: None.

I claim:

1. A new and distinct variety of calla lily plant named 'Odessa' as is herein described and illustrated.

* * * * *